United States Patent [19]

Huang

[11] Patent Number: 4,668,694
[45] Date of Patent: May 26, 1987

[54] 1-ARYLALKOXYPHENYL-PYRAZOLINES, KETONES OR ENOLES AS ANTI-INFLAMMATORY OR ANTI-ALLERGIC AGENTS

[75] Inventor: Fu-chih Huang, Leonia, N.J.

[73] Assignee: USV Pharmaceutical Corporation, Tuckahoe, N.Y.

[21] Appl. No.: 854,637

[22] Filed: Apr. 22, 1986

[51] Int. Cl.[4] .................. A61K 31/38; A61K 31/335; A61K 31/415; A61K 31/435
[52] U.S. Cl. .................................. 514/406; 514/277; 514/430; 514/449
[58] Field of Search ............................... 514/407, 406

Primary Examiner—Stanley J. Friedman

[57] ABSTRACT

This disclosure describes novel pharmaceutical compositions of matter which possess useful anti-inflammatory and anti-allergic properties, the active ingredients of said compositions of matter being compounds of the formula

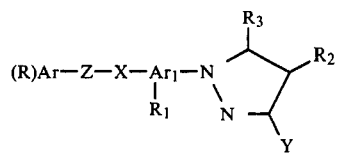

wherein
Ar and $Ar_1$ are each independently phenyl or naphthyl or a nitrogen, oxygen or sulfur-heterocyclic ring;
Z is an alkylene chain containing from 0 up to 5 carbons in the principal chain and up to a total of 7 carbons;
X is O or S;
Y is =O;
R and $R_1$ are independently hydrogen, hydroxy, lower alkoxy, lower alkanoyloxy, halo, cyano, carboloweralkoxy, carboxyloweralkyl, aryloxy or benzyloxy;
$R_2$ and $R_3$ are independently hydrogen, lower alkyl, lower aralkyl, lower alkenyl, lower alkynyl, aryl or carboxyloweralkyl and the pharmaceutically acceptable salts thereof.

6 Claims, No Drawings

1-ARYLALKOXYPHENYL-PYRAZOLINES, KETONES OR ENOLES AS ANTI-INFLAMMATORY OR ANTI-ALLERGIC AGENTS

BRIEF SUMMARY OF THE INVENTION

This invention relates to novel compositions of matter useful as lipoxygenase inhibitors and possessing anti-inflammatory and anti-allergic properties. More particularly, the present invention relates to therapeutic compositions of matter containing certain 1-arylalkoxyphenyl-pyrazolines or the pharmaceutically acceptable salts thereof which possess anti-inflammatory and anti-allergic properties. The 1-arylalkoxyphenyl-pyrazolines of the present invention may be represented by the following structural formula:

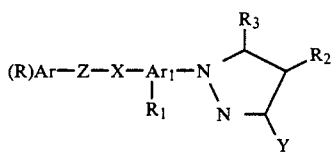

wherein

Ar and $Ar_1$ are each independently phenyl or naphthyl or a nitrogen, oxygen or sulfur-heterocyclic ring;

Z is an alkylene chain containing from 0 up to 5 carbons in the principal chain and up to a total of 7 carbons;

X is O or S;

Y is =O;

R and $R_1$ are independently hydrogen, hydroxy, lower alkoxy, lower alkanoyloxy, halo, cyano, carboloweralkoxy, carboxyloweralkyl, aryloxy or benzyloxy;

$R_2$ and $R_3$ are independently hydrogen, lower alkyl, lower aralkyl, lower alkenyl, lower alkynyl, aryl or carboxyloweralkyl.

Also included within the scope of the present invention are the tautomers thereof which may be represented by the following structural formulae wherein Ar, $Ar_1$, Z, X, R, $R_1$, $R_2$ and $R_3$ have the meanings hereinbefore given:

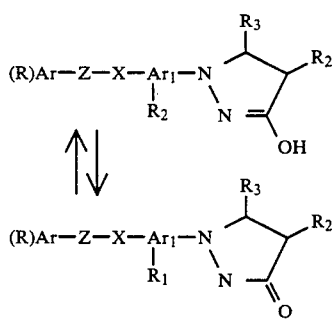

DETAILED DESCRIPTION OF THE INVENTION

The heterocyclic rings exemplary of Ar are 5-10 membered rings containing at least one oxygen, sulfur or nitrogen and include the so-called benzoheterocyclic rings. Exemplary heterocyclics include furan, thiophene, pyrrole, pyridine, thiazole, piperazine, oxazole, benzofuran, quinoline, isoquinoline, indole, benzothiophene, benzoxazole and similar heterocyclic rings as well as the N-oxides of the nitrogen-heterocyclics. The preferred heterocyclic groups are quinoline, pyridine and benzothiophene.

Additional variations in the structural formula representing the instant compounds can be effected without significantly altering the therapeutic properties, e.g., lipoxygenase inhibition. For example, the aryl groups can be substituted by one or more of a variety of substituents such as alkyl, aryl, halogen, hydroxy, alkoxy, aryloxy, such as phenoxy, benzyloxy, carboxy, carbalkoxy, carbamoyl, nitrilo, amino, alkylamino, dialkylamino, formyl, trihalomethyl and nitro groups.

The alkyl groups, either alone or within the various substituents defined hereinabove, are preferably lower alkyl, which may be straight or branchend-chain and include methyl, ethyl, propyl, isopropyl, butyl, isobutyl, amyl, hexyl, and the like.

Exemplary alkanoyl groups include acetyl, propionyl, butyryl, valeryl, isobutyryl and pivaloyl.

The halo atoms in halo and trihalomethyl are Cl, Br, I and F.

In accordance with the present invention, the preferred compounds are those in which Ar and $Ar_1$ are phenyl, quinolinyl, pyridyl or benzothiophenyl, Z is methylene, X is oxygen, $R_1$, $R_2$ and $R_3$ are hydrogen.

The compounds of the present invention may contain one or more asymmetric carbon atoms and may exist in racemic and optically active forms. All of these compounds are contemplated to be within the scope of the present invention.

The present compounds can be prepared by art recognized procedures from known compounds or readily preparable intermediates.

The active compounds of this invention may be readily prepared in accordance with the following reaction scheme:

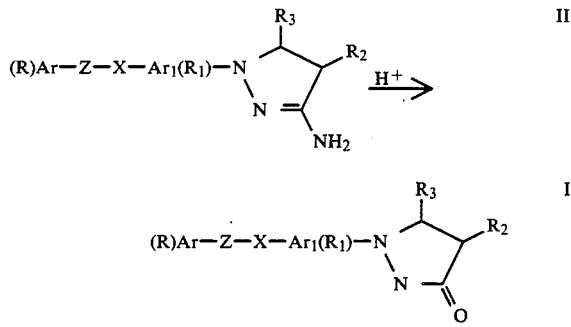

wherein (R), Ar, Z, X, $Ar_1$, ($R_1$), $R_2$ and $R_3$ have the meanings hereinbefore defined. In accordance with this reaction scheme, an appropriate 3-aminopyrazoline is treated with dilute aqueous acid, i.e. sulfuric acid, hydrochloric acid, etc. and heated to the boil for a sufficient length of time, e.g. about six hours to complete the reaction.

The active compounds may also be prepared by reacting an aryl hydrazine of Formula III with an α,β-unsaturated acid derivative of Formula IV in the presence of a strong base. An exemplary scheme is depicted below:

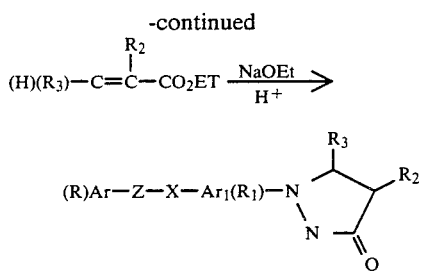

wherein (R)Ar, Z, X, Ar$_1$, R$_1$, R$_2$ and R$_3$ have the meanings hereinbefore given.

In this reaction scheme an appropriate arylhydrazine preferably in the form of a salt, e.g. the hydrochloride is reacted with a suitable acrylate, e.g. ethyl acrylate and the reaction is carried out in the presence of a base, e.g. sodium ethoxide, potassium methoxide, etc. in ethanol.

In the reactions described hereinabove, the reactions are carried out in a solvent that will dissolve the reactants and is inert to both reactants and products as well. Solvents include diethyl ether, tetrahydrofuran, dioxane, toluene, and the like. The aforesaid reactions can be carried out at or near room temperature, although temperatures from 0° C. up to the reflux temperature of the reaction mixture can be employed.

The active ingredients of the present invention have potent activity in regulating lipoxygenase and, as such, possess therapeutic value in the treatment of inflammatory conditions and allergic responses such as anaphylaxis and asthma.

Lipoxygenases in mammals have been found in the lung, platelets and white cells. They are enzymes capable of oxidizing arachidonic acid into hydroperoxyeicosatetraenoic acids (HPETEs) and their stable products hydroxyeicosatetraenoic acids (HETEs). Lipoxygenases are classified according to the position in the arachidonic acid which is oxygenated. Platelets metabolize arachidonic acid to 12-HETE, while polymorphonuclear (PMN) leukocytes contain 5 and 15 lipoxygenases. It is known that 12-HETE and 5,12-diHETE are chemotactic for human neutrophils and eosinophils, and may augment the inflammation process. 5-HETE is known to be a precursor of slow reacting substance anaphylaxis (SRS-A). The SRS family of molecules, such as leukotrienes B, C and D have been shown to be potent bronchoconstrictors (see, NATURE, 288, 484–486 (1980)).

The following protocols describe assays that detect inhibitors of the lipoxygenase. Such inhibitors are believed to be capable of modulating the biosynthesis of the leukotrienes, a property believed to be useful in treating asthma and inflammatory disease states.

The active compounds of the present invention possess the property of regulating lipoxygenase as established by the following tests.

Protocol for Detecting Inhibitors of the Lipoxygenase Pathway (5-LOX Rat PMN)

A suspension of rat neutrophils in buffer is incubated for 3 minutes at 30° C. with [$^{14}$C]-arachidonic acid (AA) and calcium ionophore A23187. Citric acid (2M) is used to quench the reaction. Following the addition of a trace amount of ($^3$H)-5-HETE together with an excess of unlabeled 5-HETE to each tube, the mixture is extracted with chloroform/methanol. The organic layer is washed with dilute acid and an aliquot is transferred to glass tubes and dried. The residue is dissolved in a small volume of chloroform and an aliquot is spotted on silica gel TLC sheets which are developed with an ethyl acetate/isooctane/water/acetic acid solvent system. The 5-HETE spots are visualized with iodine, cut out and placed in scintillation vials for counting. After adjusting the extraction efficiency, the amount (pmole) of [$^{14}$C]-5-HETE in each of the tubes is quantitated. The net pmoles of 5-HETE are obtained by substracting the pmoles of 5-HETE in the tubes containing buffer alone (blank) from the pmoles of 5-HETE in the tubes containing buffer and cells (control). The ability of the test compounds to modulate the activity of this enzyme is determined by a decrease or increase in the net amount of 5-HETE produced.

Table I below shows the concentration required for inhibition of the 5-lipoxygenase (5-LOX/I$_{50}$ um) for a representative compound according to the present invention.

Protocol for the Biosynthesis of 5-HETE (5-(S)-Hydroxyeicosatetraenoic Acid) by Human Polymorphonuclear Leukocytes in Vitro (5-LOX Human PMN)

A. Isolation of Human Neutrophils

Freshly drawn venous blood from healthy human volunteers is mixed with 2 mM ethylenediamine tetraacetic acid and is sedimented at 1×g over 6% dextran-saline. The leukocyte layer is aspirated, and the cells are concentrated by centrifugation and are layered over stacked Percoll ® solutions having densities of 1.072, 1.082 and 1.100, respectively. PMNs are isolated at the interface between the two densest layers after centrifugation at 400×g. Contaminating red blood cells are lysed by a short treatment of 0.16M ammonium chloride.

B. The Assay

A suspension of human neutrophils in buffer is incubated for 3 minutes at 30° C. with ($^{14}$C)-arachidonic acid (AA) and calcium ionophore A23187. Citric Acid (2M)/NDGA (nordihydroguaiaretic acid) (10 mM) is used to quench the reaction. Following the addition of a trace amount of ($^3$H)-5-HETE together with an excess of unlabeled 5-HETE to each tube, the mixture is extracted with chloroform/methanol. The organic layer is washed with dilute hydrochloric acid and the total volume is transferred to glass tubes and dried in vacuo. The residue is dissolved in a small volume of chloroform and is spotted on silica gel TLC sheets which are developed with an ethyl acetate/isooctane/water/acetic acid solvent system (11/5/10/1 v/v). The 5-HETE spots are visualized under UV light, cut out and placed in scintillation vials for quantitation of radioactivity. After adjusting for the extraction efficiency, the amount (pmole) of ($^{14}$C)-5-HETE in each of the tubes is calculated. The net pmoles of 5-HETE are obtained by subtracting the pmole of 5-HETE in the tubes containing buffer along (blank) from the pmoles of 5-HETE in the tubes containing buffer and cells (control). The ability of the test compound to modulate the activity of this enzyme is determined by a decrease or increase in the net amount of 5-HETE produced. This assay is a modification of that described by Bach and Brashler for rat peritoneal cells: Bach, M., Brashler, J.: Ionophore A23187-Induced Production of SRS-A by Rat Peritoneal Cells In Vitro: Evidence for Production by Mononuclear Cells, J. Immunol., 120, 998–1005 (1978).

Table I below shows the concentration required for inhibition of the 5-lipoxygenase (5-LOX/$I_{50}$ um) for a representative compound according to the present invention.

TABLE I

| Compound | Rat PMN | $I_{50}$, uM 5-LOX Human PMN |
|---|---|---|
| 1-(4-Benzyloxyphenyl)-3-pyrazolidinone | 1 | 2 |

The active ingredients of the present invention may be orally administered, for example, with an inert diluent or with an assimilable edible carrier, or they may be enclosed in hard or soft shell gelatin capsules, or they may be compressed into tablets, or they may be incorporated directly with the food of the diet. For oral therapeutic administration, the active compounds may be incorporated with excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2% to about 60% of the weight of the unit. The amount of active ingredient in such therapeutically useful compositions is such that a suitable dosage will be obtained. Preferred compositions or preparations according to the present invention are prepared so that an oral dosage unit form contains between about 5 and 200 milligrams of active compound.

The tablets, troches, pills, capsules and the like may also contain the following: A binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil or wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compond, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts employed. In addition, the active ingredients may be incorporated into sustained-release preparations and formulations.

The active ingredients of the present invention may also be administered parenterally or intraperitoneally. Solutions of the active ingredient as a free base or salt can be prepared in water suitably mixed with a surfactant such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions or manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use of the compositions of agents delaying absorption, for example, aluminum monostearate and gelatin.

Sterile injectable solutions are prepared by incorporating the active ingredient in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from a previously sterile-filtered solution thereof.

As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatable with the active ingredient, its use in the present compositions is contemplated. Supplementary active ingredients can also be incorporated into the inventive compositions.

It is especially advantageous to formulate parenteral compositions in dosage unit form for ease of administration and uniformity of dosage. Dosage unit form as used in the specification and claims herein refers to physically discrete units suited as unitary dosages for the mammalian subjects to be treated; each unit containing a predetermined quantity of active material calculated to produce the desired therapeutic effect in association with the required pharmaceutical carrier. The specification for the novel dosage unit forms of the invention are dictated by and directly dependent on (a) the unique characteristics of the active material and the particular therapeutic effect to be achieved, and (b) the limitations inherent in the art of compounding such an active material for the treatment of disease in living subjects having a diseased condition in which bodily health is impaired as disclosed in detail in this specification.

The dosage of the principal active ingredient for the treatment of the indicated conditions depends upon the age, weight and condition of the subject being treated; the particular condition and its severity; the particular form of the active ingredient and the route of administration. A daily dose of from about 5 to about 200 mg./kg. of body weight given singly or in divided doses of up to 5 times a day embraces the effective range for the treatment of most conditions for which the compound is effective and substantially non-toxic. If the dosage is divided, for example, into 3 individual dosages, these will range from about 125 mg. to about 1.0 g of the active ingredient.

The principal active ingredient is compounded for convenient and effective administration in effective amounts with a suitable pharmaceutically-acceptable carrier in dosage unit form as hereinbefore disclosed. A unit dosage form can, for example, contain the principal active ingredient in amounts ranging from about 0.1 to about 3.0 g, with from about 0.5 to about 1.0 g being preferred. Expressed in proportions, the active ingredient is generally present in from about 0.1 to about 400 mg./ml of carrier. In the case of compositions containing supplementary active ingredients, the dosages are determined by reference to the usual dose and manner of administration of said ingredients.

The invention will be described in greater detail in conjunction with the following specific examples.

EXAMPLE 1

1-(4-Benzyloxyphenyl)-3-pyrazolidinone

To a mixture of 2.5 g of 4-benzyloxyphenylhydrazine HCl and sodium ethoxide (1.6 g) in 10 ml of EtOH and 10 ml of toluene are added 1.08 of ethyl acrylate at room temperature. The reaction mixture is then heated at 85° C. overnight. The reaction mixture is evaporated to dryness under vacuum and water added to the residue and the pH adjusted to pH 6 by 1N-HCl solution. Extraction with ethyl acetate and drying the organic solution and evaporating to dryness yields 2.8 g of crude product. Purification by dry column chromatography gives 0.3 g of product; mp. 130°–134° C.

In a similar fashion according to the procedure of the preceding example, the following compounds can be prepared from appropriate starting materials:
1-(3-Benzyloxyphenyl)-3-pyrazolidinone.
1-[4-(3-Pyridylmethoxy)phenyl]-3-pyrazolidinone.
1-[3-(2-Quinolinylmethoxy)phenyl]-3-pyrazolidinone.
1-(5-Benzyloxypyridin-2-yl)-3-pyrazolidinone.

EXAMPLE 2

| Per Tablet | Preparation of 50 mg. Tablets | Per 10,000 Tablets |
| --- | --- | --- |
| 0.050 gm. | 1-4-Benzyloxyphenyl-3-pyrazolidinone | 500 gm. |
| 0.080 gm. | Lactose | 800 gm. |
| 0.010 gm. | Corn Starch (for mix) | 100 gm. |
| 0.008 gm. | Corn Starch (for paste) | 75 gm. |
| 0.148 gm. | | 1475 gm. |
| 0.002 gm. | Magnesium Stearate (1%) | 15 gm. |
| 0.150 gm. | | 1490 gm. |

The 1-4-benzyloxyphenyl-3-pyrazolidinone, lactose and corn starch (for mix) are blended together. The corn starch (for paste) is suspended in 600 ml. of water and heated with stirring to form a paste. This paste is then used to granulate the mixed powders. Additional water is used if necessary. The wet granules are passed through a No. 8 hand screen and dried at 120° F. The granules are then passed through a No. 16 screen. The mixture is lubricated with 1% magnesium stearate and compresed into tablets in a suitable tableting machine.

EXAMPLE 3

| Preparation of Oral Suspension | |
| --- | --- |
| Ingredient | Amount |
| 1-4-Benzyloxyphenyl-3-pyrazolidinone | 500 mg. |
| Sorbitol solution (70% N.F.) | 40 ml. |
| Sodium benzoate | 150 mg. |
| Saccharin | 10 mg. |
| Red dye | 10 mg. |
| Cherry flavor | 50 mg. |
| Distilled water qs ad | 100 ml. |

The sorbiton solution is added to 40 ml. of distilled water and the 1-4-benzyloxyphenyl-3-pyrazolidinone is suspended therein. The saccharin, sodium benzoate, flavor and dye are added and dissolved. The volume is adjusted to 100 ml. with distilled water. Each ml. of syrup contains 5 mg. of 1-4-benzyloxyphenyl)-3-pyrazolidinone.

EXAMPLE 4

Preparation of Parenteral Solution

In a solution of 700 ml. of propylene glycol and 200 ml. of water for injection is suspended 20.0 grams of 1-4-benzyloxyphenyl)-3-pyrazolidinone with stirring. After suspension is complete, the pH is adjusted to 5.5 with hydrochloric acid and the volume is made up to 1000 ml. with water for injection. The formulation is sterilized, filled into 5.0 ml. ampoules each containing 2.0 ml. (representing 40 mg. of drug) and sealed under nitrogen.

What is claimed is:

1. A method of treating inflammatory conditions of allergic responses in a mammal comprising administering to said mammal an effective amount of a compound selected from the group consisting of those of the formula

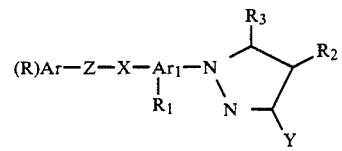

wherein

Ar and $Ar_1$ are each independently phenyl or naphthyl

Z is an alkylene chain containing from 0 up to 5 carbons in the principal chain and up to a total of 7 carbons;

X is O or S;

Y is =O;

R and $R_1$ are independently hydrogen, hydroxy, lower alkoxy, lower alkanoyloxy, halo, cyano, carboloweralkoxy, carboxyloweralkyl, aryloxy or benzyloxy;

$R_2$ and $R_3$ are independently hydrogen, lower alkyl, lower aralkyl, lower alkenyl, lower alkynyl, aryl or carboxyloweralkyl and the pharmaceutically acceptable salts thereof.

2. The method according to claim 1 in which the compound is 1-(4-benzyloxyphenyl)-3-pyrazolidinone.

3. The method according to claim 1 in which the compound is 1-(3-benzyloxyphenyl)-3-pyrazolidinone.

4. A pharmaceutical composition in dosage unit form comprising an effective therapeutic dose for treatment of inflammatory conditions of allergic responses in a mammal of a compound selected from the group consisting of those of the formula:

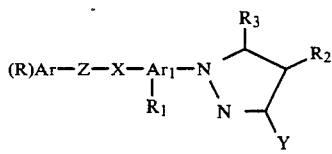

wherein

Ar and Ar$_1$ are each independently phenyl or naphthyl;

Z is an alkylene chain containing from 0 up to 5 carbons in the principal chain and up to a total of 7 carbons;

X is O or S;

Y is =O;

R and R$_1$ are independently hydrogen, hydroxy, lowre alkoxy, lower alkanoyloxy, halo, cyano, carboloweralkoxy, carboxyloweralkyl, aryloxy or benzyloxy;

R$_2$ and R$_3$ are independently hydrogen, lower alkyl, lower aralkyl, lower alkenyl, lower alkynyl, aryl or carboxyloweralkyl and the pharmaceutically acceptable salts thereof, in association with a pharmaceutical carrier.

5. A composition of matter according to claim 4 wherein the compound is 1-(4-benzyloxyphenyl)-3-pyrazolidinone.

6. A composition of matter according to claim 4 wherein the compound is 1-(3-benzyloxyphenyl)-3-pyrazolidinone.

* * * * *